(12) United States Patent
Forster (10) Patent No.: US 8,760,295 B2
(45) Date of Patent: Jun. 24, 2014

(54) APPARATUS AND METHODS FOR TREATING A WOUND

(75) Inventor: Ian J. Forster, Essex (GB)

(73) Assignee: Avery Dennison Corporation, Glendale, CA (US)

( * ) Notice: Subject to any disclaimer, the term of this patent is extended or adjusted under 35 U.S.C. 154(b) by 603 days.

(21) Appl. No.: 12/560,577

(22) Filed: Sep. 16, 2009

(65) Prior Publication Data

US 2010/0161009 A1   Jun. 24, 2010

Related U.S. Application Data

(63) Continuation-in-part of application No. 12/339,736, filed on Dec. 19, 2008.

(51) Int. Cl.
*G08B 13/14* (2006.01)
*G08B 1/08* (2006.01)
*G08B 23/00* (2006.01)
*H04B 3/00* (2006.01)

(52) U.S. Cl.
USPC ............... 340/572.1; 340/572.4; 340/572.8; 340/539.1; 340/539.11; 340/693.1; 340/693.2; 340/425.2

(58) Field of Classification Search
USPC ........... 340/10.1–10.6, 572.1–57.9, 5.1–5.92
See application file for complete search history.

(56) References Cited

U.S. PATENT DOCUMENTS

| | | | |
|---|---|---|---|
| 4,202,491 A | 5/1980 | Suzuki | |
| 4,656,463 A * | 4/1987 | Anders et al. | ............... 340/573.4 |
| 5,874,724 A | 2/1999 | Cato | |
| 6,290,713 B1 * | 9/2001 | Russell | ........................... 607/88 |
| 6,335,685 B1 | 1/2002 | Schrott et al. | |
| 6,677,852 B1 | 1/2004 | Landt | |
| 6,830,181 B1 | 12/2004 | Bennett | |
| 7,002,474 B2 | 2/2006 | De Souza et al. | |
| 7,085,497 B2 * | 8/2006 | Tiemann et al. | ............. 398/107 |
| 7,146,147 B1 * | 12/2006 | Sabatino | ....................... 455/300 |

(Continued)

FOREIGN PATENT DOCUMENTS

| | | |
|---|---|---|
| EP | 1755074 | 2/2007 |
| EP | 1962232 | 8/2008 |

(Continued)

OTHER PUBLICATIONS

International search report and written opinion issued in corresponding International application PCT/US2009/066973 dated Feb. 19, 2010.

(Continued)

*Primary Examiner* — Steven Lim
*Assistant Examiner* — Muhammad Adnan
(74) *Attorney, Agent, or Firm* — Avery Dennison Corporation (57) ABSTRACT

A wound dressing includes a substrate, an optical energy emitting device, and a radio frequency receiving device. The substrate is configured to engage biological tissue of a patient. The optical energy emitting device is attached to the substrate, and the radio frequency receiving device is electrically coupled with the optical energy emitting device. The radio frequency receiving device is configured to capture energy from radio frequency transmissions. The radio frequency receiving device is further configured to direct at least a portion of the energy to the optical energy emitting device. Upon receipt of the energy from the radio frequency receiving device, the optical energy emitting device is configured to emit light onto biological tissue of a patient.

20 Claims, 7 Drawing Sheets

(56) References Cited

U.S. PATENT DOCUMENTS

| | | | |
|---|---|---|---|
| 7,199,719 | B2 | 4/2007 | Steinberg |
| 7,229,023 | B2 | 6/2007 | Raaskar |
| 7,295,117 | B2 | 11/2007 | Forster et al. |
| 7,323,614 | B2 * | 1/2008 | Lerat et al. .................. 602/48 |
| 7,425,899 | B2 | 9/2008 | Stewart et al. |
| 7,513,431 | B2 | 4/2009 | Chiu |
| 7,982,601 | B2 | 7/2011 | Corrado et al. |
| 8,449,587 | B2 * | 5/2013 | Cornil ........................ 607/89 |
| 2004/0012496 | A1 | 1/2004 | De Souza et al. |
| 2004/0027495 | A1 * | 2/2004 | Ferris ........................ 348/734 |
| 2004/0100834 | A1 | 5/2004 | Waters |
| 2004/0125074 | A1 * | 7/2004 | Lin ............................ 345/156 |
| 2005/0012616 | A1 | 1/2005 | Forster et al. |
| 2005/0029350 | A1 | 2/2005 | Jusas et al. |
| 2005/0212673 | A1 | 9/2005 | Forster |
| 2005/0221752 | A1 * | 10/2005 | Jamieson et al. .............. 455/1 |
| 2005/0258939 | A1 | 11/2005 | Kantrowitz et al. |
| 2006/0012387 | A1 | 1/2006 | Shanks |
| 2006/0055552 | A1 | 3/2006 | Chung et al. |
| 2006/0173514 | A1 * | 8/2006 | Biel et al. ..................... 607/88 |
| 2006/0202802 | A1 | 9/2006 | Sepp |
| 2006/0255140 | A1 | 11/2006 | Jusas et al. |
| 2006/0261951 | A1 | 11/2006 | Koemer et al. |
| 2007/0040683 | A1 | 2/2007 | Oliver et al. |
| 2007/0132592 | A1 | 6/2007 | Stewart et al. |
| 2007/0233208 | A1 * | 10/2007 | Kurtz et al. .................... 607/88 |
| 2008/0171957 | A1 * | 7/2008 | Connolly et al. .............. 602/42 |
| 2008/0174436 | A1 | 7/2008 | Landt et al. |
| 2009/0207582 | A1 | 8/2009 | Dorsey et al. |

FOREIGN PATENT DOCUMENTS

| | | |
|---|---|---|
| GB | 2410151 | 7/2005 |
| JP | 2005196445 | 7/2005 |
| WO | 2010019286 | 2/2010 |

OTHER PUBLICATIONS

Response to International search report and written opinion filed in corresponding International application PCT/US2009/066973 on May 4, 2010.

International preliminary report on patentability issued in corresponding International application PCT/US2009/066973 dated Jun. 30, 2011.

Semitracks, Inc., What is Light Induced Voltage Alteration? Http://semitracks.com/reference/FA/die_level/optical/liva/liva.htm, Sep. 4, 2008, 12 pages.

* cited by examiner

APPARATUS AND METHODS FOR TREATING A WOUND

CROSS-REFERENCE TO RELATED APPLICATION

This application is a continuation-in-part of Ser. No. 12/339,736 filed on Dec. 19, 2008 entitled Optical Control of RFID Chips, which application is assigned to the same assignee as this application and whose disclosure is incorporated by reference herein.

TECHNICAL FIELD OF THE INVENTION

The disclosed apparatus and methods relate generally to wound dressings and more particularly to wound dressings that administer a therapeutic treatment to a wound.

BACKGROUND OF THE INVENTION

Typically a wound to the flesh or tissue includes a portion of the wound that is open or exposed to the surrounding environment. It is common to place a bandage or other type of dressing over the open and exposed portion of the wound to protect the wound from the environment. Despite such protective measures, bacteria and other such harmful organisms, e.g. virus or fungal, often enter the wound through the open and exposed portion of the wound and result in infection and other such harmful effects. To combat these harmful situations, wounds are commonly administered therapeutic treatments by periodically removing a protective dressing from the wound, applying an anti-bacterial or fungal creams, mendicants or ointments to the wound, and positioning a new dressing over the wound. The process may be repeated over and over depending on the severity of the wound, the environment in which the patient is being treated as well as the health of the patient. Repeatedly redressing a wound can be painful for the patient; can increase the chance of infection and the cost associated with treating the patient.

SUMMARY OF THE INVENTION

In accordance with one embodiment, a wound dressing comprises a substrate, an optical energy emitting device, and a radio frequency receiving device. The substrate is configured to engage biological tissue of a patient. The optical energy emitting device is attached to the substrate, and the radio frequency receiving device is electrically coupled with the optical energy emitting device. The radio frequency receiving device can capture energy from radio frequency transmissions. The radio frequency receiving device can be further configured to control delivery of energy to the optical energy emitting device. Delivery of energy may be associated with a specific command or may commence when the energy captured from the radio frequency transmissions exceeds a pre-determined threshold. The energy delivered may come from the radio frequency energy received by the device or alternately may come from a storage device incorporated in the wound dressing. The storage device may be a battery or capacitor, and the storage device may be rechargeable from the radio frequency energy received. Upon receipt of the energy from the radio frequency receiving device, the optical energy emitting device is configured to emit light onto biological tissue of a patient.

In accordance with another embodiment, the optical energy is directed onto a material incorporated into the dressing that generates an effect detrimental to undesirable biological entities such as viruses, bacteria and fungi.

In accordance with another embodiment, a substrate comprises an adhesive layer configured to removably secure a wound dressing to biological tissue of a patient.

In accordance with another embodiment, an optical energy emitting device comprises a light emitting diode.

In accordance with another embodiment, a light emitting diode is configured to emit ultraviolet light.

In accordance with another embodiment, an optical energy emitting device is configured to emit one of more wavelengths in the range 10 nm to 10 μm.

In accordance with another embodiment, an optical energy emitting device comprises an array of light emitting diodes arranged in a matrix.

In accordance with another embodiment, a radio frequency receiving device comprises a radio frequency identification tag comprising a memory device.

In accordance with another embodiment, a memory device is configured to store data corresponding to energy directed from a radio frequency receiving device to an optical energy emitting device.

In accordance with another embodiment, a radio frequency receiving device is configured to selectively direct energy to an optical energy emitting device in response to data stored in the memory device.

In accordance with another embodiment, a wound dressing comprises a biological sensor attached to a substrate and electrically coupled with a radio frequency receiving device.

In accordance with another embodiment, a biological sensor is configured to sense a level of bacteria, virus, fungi or other undesirable biological entity present on biological tissue of a patient proximate to the biological sensor.

In accordance with another embodiment, a biological sensor is configured to facilitate direction of energy from a radio frequency receiving device to an optical energy emitting device when a level of bacteria, virus, fungi or other undesirable biological entity sensed by the biological sensor is above a threshold level.

In accordance with another embodiment, a wound treatment system comprises a radio frequency transceiver and a wound treatment dressing. The radio frequency transceiver is configured to generate radio frequency transmissions. The wound treatment dressing is remotely positioned from the radio frequency transceiver and comprises a substrate, an optical energy emitting device, and a radio frequency receiving device. The substrate is configured to engage biological tissue of a patient. The optical energy emitting device is attached to the substrate, and the radio frequency receiving device is electrically coupled with the optical energy emitting device. The radio frequency receiving device is configured to capture energy from the radio frequency transmissions or to utilize energy contained in a storage device such as a battery or capacitor and further configured to direct at least a portion of the energy to the optical energy emitting device. Upon receipt of the energy from the radio frequency receiving device, the optical energy emitting device is configured to emit light onto biological tissue of a patient.

In accordance with another embodiment, a radio frequency receiving device comprises a radio frequency identification tag comprising a memory device.

In accordance with another embodiment, a memory device is configured to store an identifying marker for a radio frequency identification tag and to transmit the identifying marker to a radio frequency transceiver in response to a radio frequency transmission.

In accordance with another embodiment, a radio frequency receiving device is configured to transmit data to a radio frequency transceiver in response to a radio frequency transmission. The data corresponds to energy directed from the radio frequency receiving device to an optical energy emitting device. The radio frequency transceiver is configured to collect and associate the data with a radio frequency identification tag.

In accordance with another embodiment, a method is provided for treating a wound. The method comprises positioning a wound treatment dressing proximate to biological tissue of a patient. The wound treatment dressing comprises a substrate, an optical energy emitting device attached to the substrate, and a radio frequency receiving device electrically coupled with the optical energy emitting device. The method further comprises positioning a radio frequency transceiver within signal range of the wound treatment dressing, and generating a radio frequency transmission with the radio frequency transceiver. Additionally, the method comprises the radio frequency receiving device capturing energy from the radio frequency transmissions or utilizing previously stored energy from a battery or capacitor to facilitate energizing of the radio frequency receiving device, and directing at least a portion of the energy from the radio frequency receiving device to the optical energy emitting device such that the optical energy emitting device emits light through the substrate and onto biological tissue of a patient.

In accordance with another embodiment, a method for treating a wound comprises storing data within at least one of a radio frequency receiving device and a radio frequency transceiver. The data corresponds to past instances of directing energy from the radio frequency receiving device to an optical energy emitting device.

In accordance with another embodiment, a method for treating a wound comprises selectively directing energy from a radio frequency receiving device to an optical energy emitting device in response to data.

In accordance with another embodiment, a method for treating a wound comprises storing an identifying marker within a radio frequency receiving device and selectively transmitting the identifying marker from the radio frequency receiving device to a radio frequency transceiver in response to a radio frequency transmission.

In accordance with another embodiment, a method for treating a wound comprises sensing a level of harmful organisms, e.g. bacteria, virus or fungus in the wound and comparing the sensed level of organisms in the wound with a threshold level of the organism. Energy is directed from a radio frequency receiving device to at least one optical energy emitting device only when the sensed level of bacteria in the wound is above the threshold level of bacteria.

BRIEF DESCRIPTION OF THE DRAWINGS

It is believed that certain examples will be better understood from the following description taken in combination with the accompanying drawings in which.

DETAILED DESCRIPTION OF THE INVENTION

The apparatus and methods disclosed in this document are described in detail by way of examples and with reference to the figures. Unless otherwise specified, like numbers in figures indicate references to the same, similar, or corresponding elements throughout the figures. Those of ordinary skill in this art will recognize that modifications to disclosed and described embodiments, components, elements, arrangements, methods, materials, etc. can be made and may be desired for a specific application. In this disclosure, any identification of specific shapes, materials, techniques, arrangements, and the like are either related to a specific example presented or are merely a general description of such a shape, material, technique, arrangement, etc. Identifications of specific details or examples are not intended to be and should not be construed as mandatory or limiting unless specifically designated as such. Selected examples of apparatuses and methods for therapeutically treating a wound are hereinafter disclosed and described in detail with reference made to FIGS. 1-7.

Figure 1:
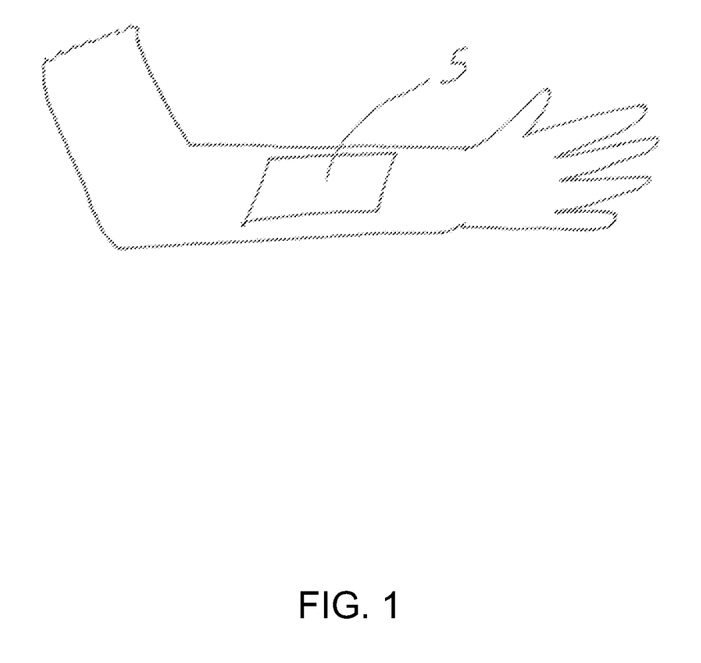
FIG. 1 is schematic view depicting a wound dressing applied to a human forearm.

Through the course of normal activity, humans, animals, and other such biological beings commonly sustain injuries or other such damage to exterior surfaces such as skin or the biological tissue under the skin. Such injuries are commonly referred to as wounds. As illustrated in FIG. 1, such wounds can be covered or otherwise protected by a dressing 5 that forms a barrier to the entry of dirt and bacteria into the wound and facilitates healing of the wound. As will be disclosed herein, a wound dressing can be arranged to provide therapeutic treatment to the wound. In one example, a wound dressing can provide anti-bacterial, anti-viral or anti-fungal treatments to a wound. In another example, the wound dressing can be configured to provide therapeutic treatments to the wound by positioning optical energy emitting devices that emit anti-bacterial light such that the emitted light is directed toward the wound, or towards a secondary material or area that generates a therapeutic effect, such as an area containing particles of titanium dioxide which can generate free radicals when exposed to UV light or an area where the UV light creates ozone by interaction with oxygen.

Figure 2:
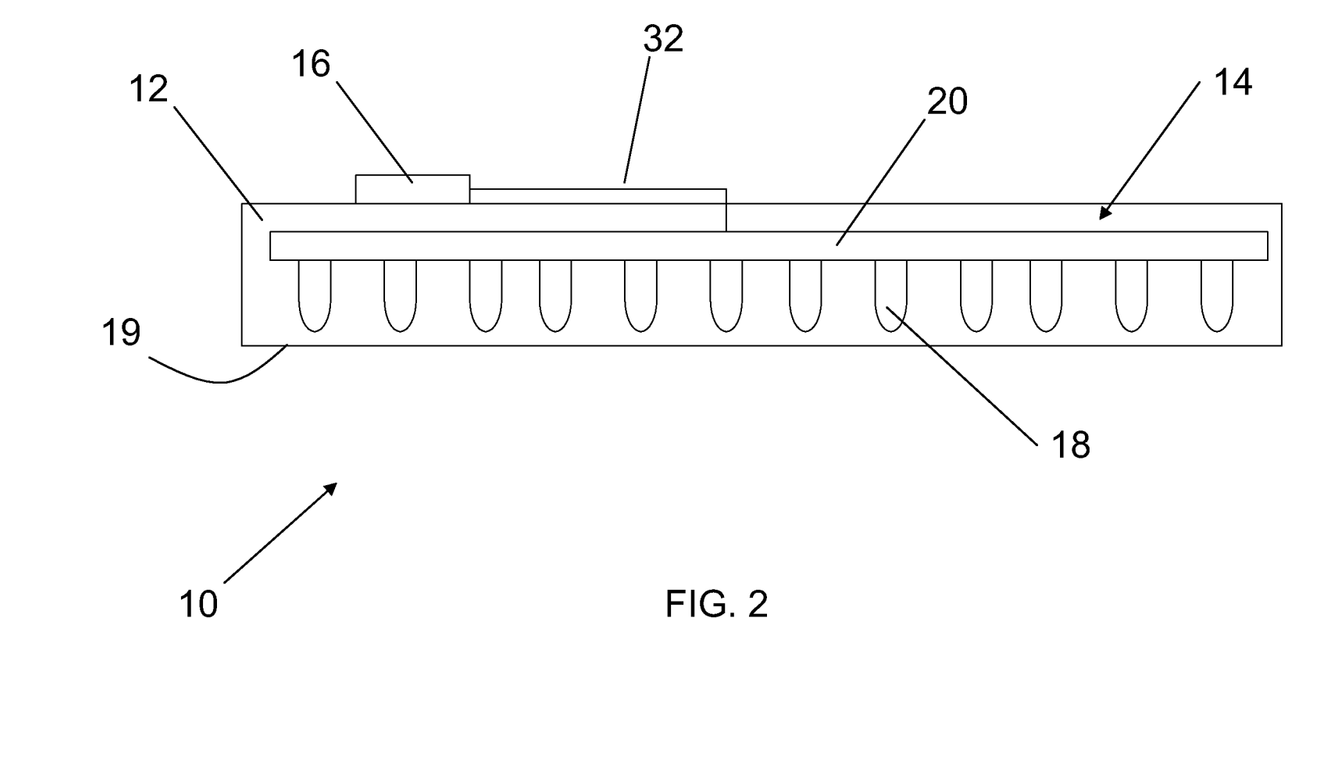
FIG. 2 is a schematic cross-sectional view depicting a wound dressing in accordance with an embodiment.

An embodiment of a wound dressing 10 configured to administer therapeutic treatments to a wound is schematically illustrated in FIG. 2. In this embodiment, the wound dressing 10 comprises a substrate 12, an optical energy emitting device 14, and a radio frequency receiving device 16. The optical energy emitting device 14 can be attached to or otherwise coupled to the substrate 12 so that the positioning and orientation of the optical energy emitting device 14 is generally determined by the positioning and orientation of the substrate 12. In one example, the optical energy emitting device 14 comprises a series or array of light emitting diodes (LED) 18 mounted to a further substrate with a suitable conductor pattern to interconnect the LED's 20. Alternatively a single diode with a suitable disperser can be used to ensure even delivery of optical energy. In a further embodiment the optical energy is launched into a substantially transparent or other material which acts as a waveguide, for example an optical fiber, absorbent or reflective material, with points defined on the waveguide structure that scatter light towards the wound area.

As shown in FIG. 2, the LEDs 18 and circuit board 20 can be embedded in the substrate 12. It will be appreciated that by such embedment the positioning of the LEDs 18 cab be determined by the positioning of the substrate 12. The substrate 12 can be arranged so that an exterior surface 19 of the substrate 12 engages a wound or the skin or tissue proximate to a wound. When so engaged, the exterior surface 19 of the substrate 12 and, thus, the LEDs 18 can be positioned above and proximate to the wound.

In one embodiment, the substrate 12 can comprise gauze, plastic, films, fibrous material or other material. Such materials allow for light emitted from LEDs 18 embedded in the substrate 12 to pass through the substantially transparent substrate 12. It will be understood that when the substrate 12 is positioned above and proximate to a wound, light emitted from the LEDs 18 can be directed toward the wound. Gauze is typically a layered material. Therefore, in one example, the optical energy emitting device 14 can be embedded into a substrate 12 by placing the optical energy emitting device 14 between two layers of gauze. In another example, an optical energy emitting device 14 can be embedded into a plastic substrate or film 12 during a molding or extrusion process. In yet another example, the optical energy emitting device 14 can be embedded into a substrate by placing the optical energy emitting device 14 between two sheets of plastic, such as might arise during extrusion or by softening localized regions or areas of the films or substrate, by for example heat, so that the device 14 can be embedded into the softened area.

When a substrate 12 is made from gauze, plastic, films, or other such materials, it will be readily understood that the substrate 12 can be well-suited for direct engagement with a wound. This includes direct engagement with any biological material on the surface of the wound or exiting the wound such as blood, loose tissue, discharge, and the like. That is, the materials will be sterile and will not introduce additional elements to the wound area that may be harmful.

Although optical energy emitting devices 14 have been described and illustrated as being embedded in a substrate 12, it will be understood by those skilled in the art that other arrangements and configurations are possible. For example, an optical energy emitting device can be placed or secured on a surface of a substantially transparent substrate that is opposite a substrate surface that engages the wound. In such an example, light emitted from an optical energy emitting device can be directed to pass through the substrate and into the wound. In another example, an optical energy emitting device can be placed or secured on a surface of a substrate that is positioned closest to a wound. In such an example, an additional barrier layer such as gauze or plastic sheeting can be placed between the optical energy emitting device and the wound. As will be understood, in such an example the substrate would not need to be transparent or substantially transparent in order for light to be directed into the wound. In a further embodiment the optical emitters can be printed, for example OLED (organic light emitting diode or device) devices.

Figure 3:
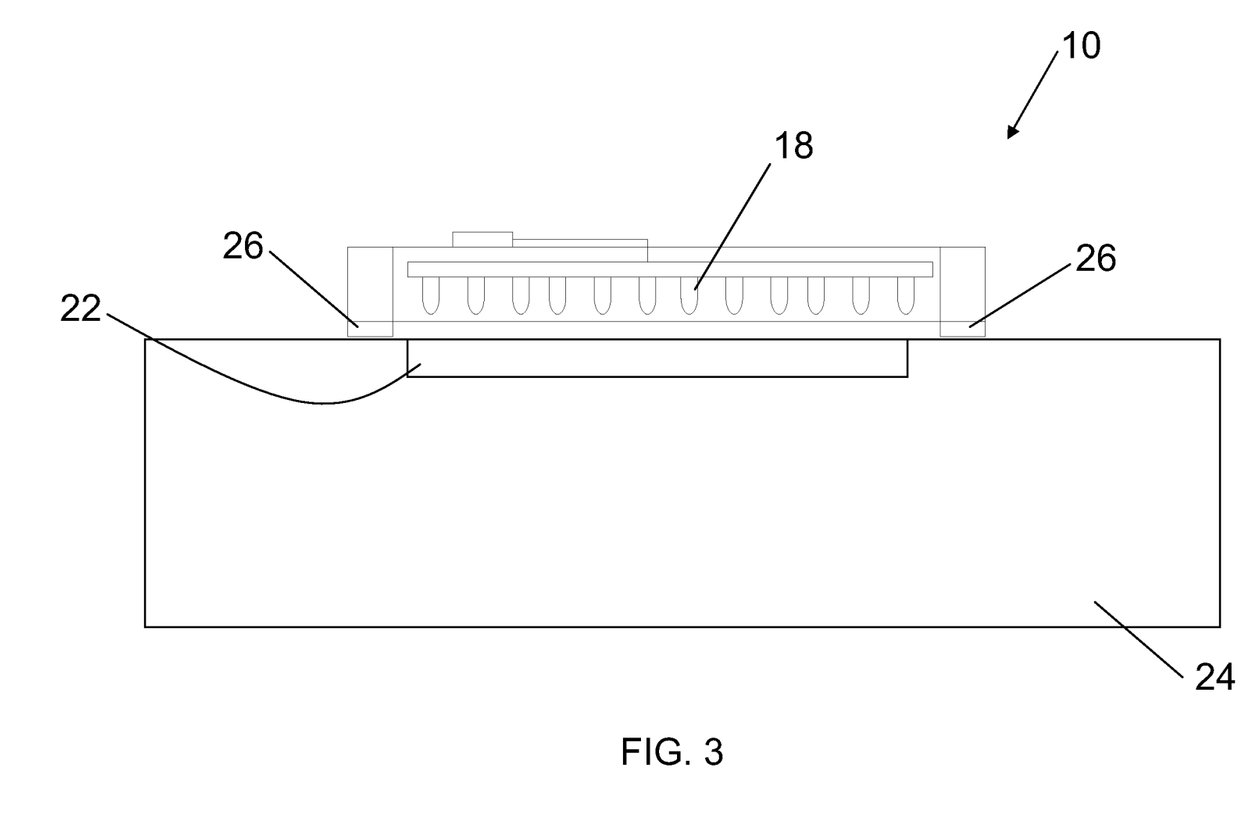
FIG. 3 is a schematic cross-sectional view depicting the wound dressing of FIG. 2 secured to biological tissue of a human body.

In one embodiment, the wound dressing 10 can be positioned and secured above and proximate to a wound by the use of adhesives. FIG. 3 schematically illustrates a wound dressing 10 secured above and proximate to a wound 22 on the surface of a human body 24. The wound dressing 10 includes an adhesive layer 26 for removably securing the wound dressing 10 above a wound 22. As is shown, by positioning the wound dressing 10 above the wound 22, the light emitted form the LEDs 18 can be directed toward the wound 22. Therefore, when the LEDs 18 emit an anti-bacterial, anti-viral or anti-fungal light, the light can be directed toward the wound 22 to administer a therapeutic anti-bacterial, anti-viral or anti-fungal treatment to the wound 22. By directing light toward the wound 22, anti-bacterial, anti-viral or anti-fungal treatment can be applied to the wound 22 itself as well as the surrounding biological tissue that can also contain harmful organisms.

Figure 4:
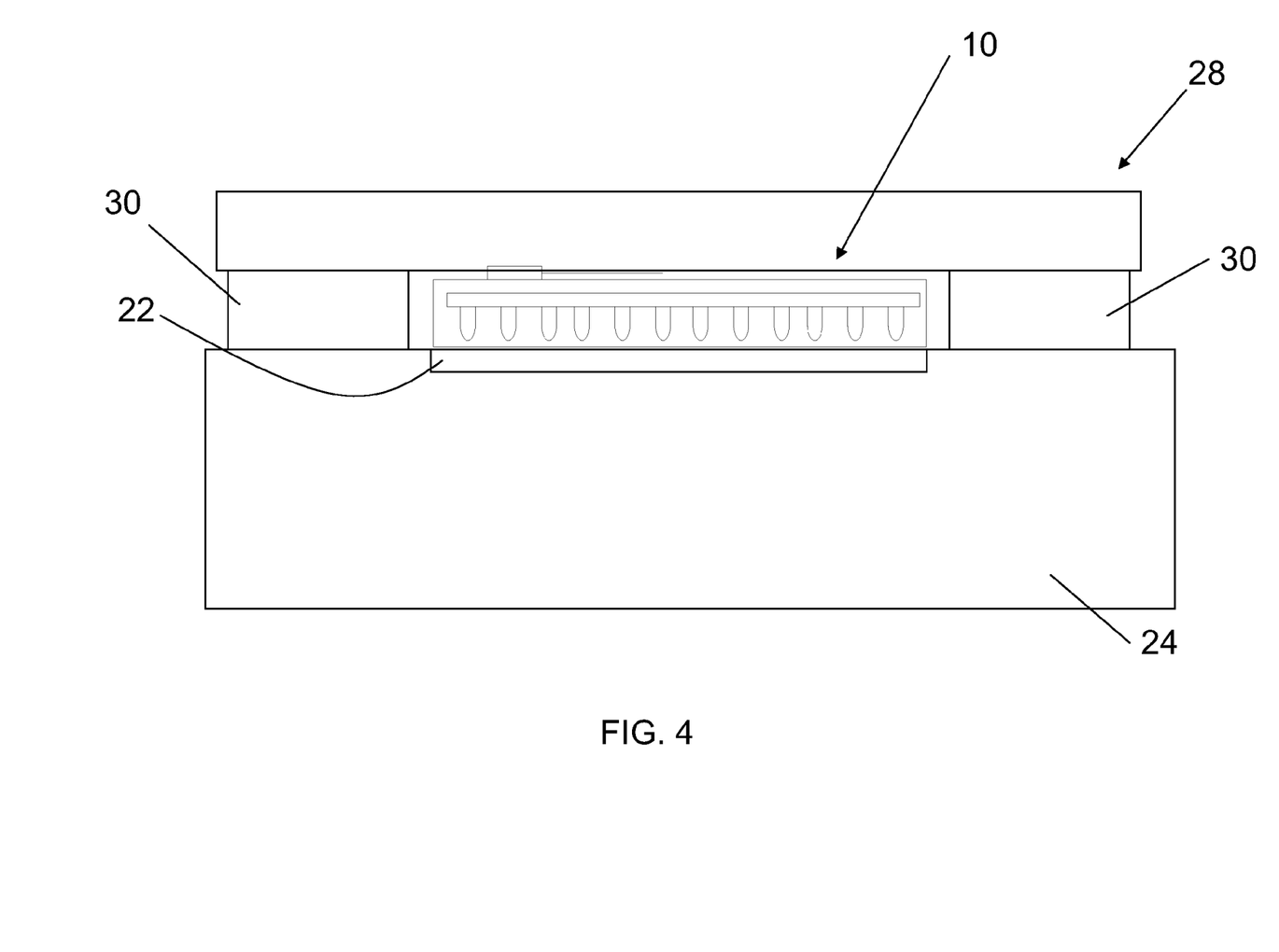
FIG. 4 is a schematic cross-sectional view depicting the wound dressing of FIG. 2 secured to biological tissue of a human body with a bandage.

In another embodiment, the wound dressing 10 can be removably secured above a wound by an adhesive bandage. FIG. 4 schematically illustrates a wound dressing 10 secured above a wound 22 by a bandage 28 that includes an adhesive layer 30. In one example, the wound dressing 10 and the bandage 28 can be secured together such that they function as one assembly. In another example, the wound dressing 10 and bandage 28 can be separate components. In this example, the wound dressing 10 is placed at a desired position, and the bandage 28 is secured over the wound dressing 10 to hold the wound dressing 10 at the desired position.

Referring again to FIG. 2, in one embodiment, the wound dressing 10 includes a radio frequency receiving device 16 configured to be electrically coupled to the optical energy emitting device 14. This is to say that the radio frequency receiving device 16 is configured to direct energy to the optical energy emitting device 14. In one example, the radio frequency receiving device 16 can direct such energy to the optical energy emitting device 14 in the form of electrical current. A metal wire 32 or other such connection can electrically couple the radio frequency receiving device 16 to the optical energy emitting device 14. One end of the metal wire 32 can be physically connected to the radio frequency receiving device 16, and the other end of the metal wire 32 can be physically connected to the optical energy emitting device 14. The metal wire 32, can form part of the antenna that allows radio frequency receiving device 16 to communicate to a radio frequency transceiver. As will be further described, the radio frequency receiving device 16 can be configured to capture energy from radio frequency transmissions or signals or utilize energy from a storage device such as a battery or capacitor that may be supplied with the structure. Once such energy is captured, a least a portion of the energy can be directed from the radio frequency receiving device 16 to the optical energy emitting device 14. Alternatively the energy directed towards the optical device could come from a storage device such as a battery or capacitor, and said battery or capacitor may be charged by rectified radio frequency energy received by device 16. Such energy can be used to stimulate the optical energy emitting device 14 such that the optical energy emitting device 14 emits light.

Figure 5:
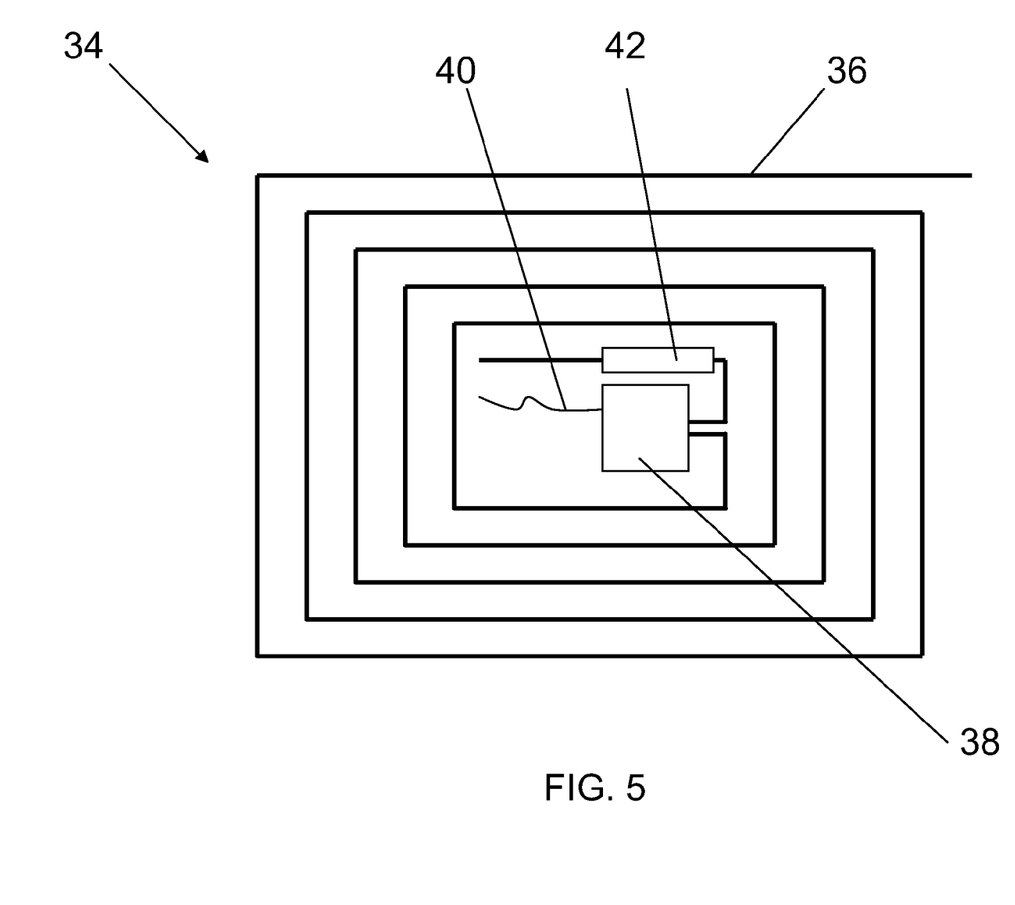
FIG. 5 is a schematic plan view depicting an RFID tag in accordance with the embodiment of FIG. 2.

In one embodiment, the radio frequency receiving device 16 can be a radio frequency identification device, commonly referred to as an RFID tag. As schematically illustrated in FIG. 5, an RFID tag 34 can comprise an antenna 36 and a rectifier 38 by which the radio frequency transmissions or signals can be received and the energy of the radio frequency transmissions can be captured. The RFID tag 34 can also include a wire or lead 40 by which energy can be directed from the RFID tag 34 to the optical energy emitting device 14. It will be understood that the lead 40 can be the same as or similar to the metal wire 32 illustrated in FIG. 2. RFID tags are available from Avery Dennison RFID Company of Clinton, S.C.

Radio frequency transmissions can be received by the antenna 36. Energy can also be stored if a storage device is provided such as through a battery or capacitor. The rectifier 38 can condition the energy of the received radio frequency transmission into an electrical current suitable for powering the optical energy emitting device 14. Therefore, it will be understood that after energy is captured by the RFID tag 34, the energy can be directed in whole or in part to the optical energy emitting device 14 to cause the optical energy emitting device 14 to emit light. As it will be additionally understood, when the wound dressing 10 is engaged with or positioned proximate to a wound, light emitted from the optical energy emitting device 14 can be directed onto or into the wound of a patient to administer therapeutic treatment to the wound.

As seen throughout the figures, an optical energy emitting device 14 can include a plurality of individual light emitting devices such as LEDs 18. In one embodiment, LEDs 18 can be arranged in a matrix configuration so that light emitted from the LEDs 18 is distributed uniformly over an area such as a wound opening. In such a configuration, a therapeutic treatment such as an anti-bacterial treatment can be applied uniformly to a wound. In another example, LEDs 18 can be configured so that ultraviolet light is emitted from the LEDs 18. In yet another example, LEDs 18 can be configured so that blue light is emitted from the LEDs 18. LEDs 18 or any other optical energy emitting device can be configured or arranged in any number of suitable configurations so that light of varying wavelengths is emitted to effectively and safely apply anti-bacterial treatments to a wound or other such biological tissue.

As will be understood, when a wound dressing 10 is arranged or positioned over a wound, the wound dressing 10 can be configured to administer treatments to the wound using a variety of methods. As previously described, in one embodiment, the RFID tag 34 directs energy in the form of an electric current to LEDs 18. The LEDs 18 emit ultraviolet, blue, or other such bactericidal, fungicidal, etc. light to administer treatment to a wound. The apparatus and methods for applying such treatments can be arranged so that each individual treatment and multiple treatments in the aggregate are controlled to produce an effective and safe treatment regimen. That is to say that the apparatus and methods can be arranged so that administered treatments are generally effective in providing therapeutic benefit to a patient and administered in a manner that is generally safe for a patient.

The administration of such light energy treatments can be associated with traditional ointments or creams or can be used to increase the operative action of such creams or ointments. For example, a layer of material containing $TiO_2$ undergoes a photo-catalytic effect under UV irradiation, generating free radicals that have strong anti-bacterial effects. Photocatalytic activity (PCA) is the ability of a material to create an electron hole pair as a result of exposure to ultraviolet radiation. The resulting free-radicals are very efficient oxidizers of organic matter. Alternatively, an ointment or spray may be applied to the wound that has two states; an inactive state, where it does not substantially effect a bacterial, fungal or viral agent, and an active state, where it provides a desired effect. The transition between these two states is effected by illumination from the source contained in the would dressing.

Examples of methods for controlling treatments can include monitoring a treatment and recording information related to that treatment. In one embodiment, when a first treatment is administered, the first treatment can be monitored and the point in time at which the first treatment is administered can be recorded. A second treatment is administered only after a predetermined amount of time has passed since the administration of the first treatment. The predetermined amount of time can be based on treatment regimens or protocols that have been proven to be effective and safe. Therefore, the predetermined amount of time can vary depending on factors such as type of wound, size of wound, intensity of treatment, duration of treatment, etc.

One embodiment of such a method includes a memory portion or device. As seen in FIG. 5, an integrated circuit 42 can be incorporated into the RFID tag 34. An integrated circuit 42 can be configured to store or record data and information, process such data and information, and modulate and demodulate a radio frequency signal to relay such data and information. As will be understood, RFID tags 34 equipped with integrated circuits 42 or other such memory devices can be arranged to dynamically store data or information. Therefore, each time a wound dressing 10 administers a treatment, the integrated circuit 42 can store data corresponding to the treatment. More specifically, the integrated circuit 42 can store data and information corresponding to the energy directed to the optical energy emitting device 14 by the RFID tag 34. For example, the data stored by the integrated circuit 42 can include the specific time the treatment was initiated, the duration of the treatment, the amount of energy directed from the RFID tag 34 to the optical energy emitting device 14, the number of treatments administered, date of application of the dressing to the patient, expiration information and the like.

Once such data is stored, additional treatments can be administered based on the stored data. For example, even though radio frequency transmissions or signals may be frequently or even continuously accessible to an RFID tag 34, the RFID tag 34 might not frequently or continuously access the radio frequency transmission to capture energy and direct that energy to an optical energy emitting device 14. Instead the data stored on the RFID tag 34 can be evaluated to determine when an additional treatment is to be administered based on a predetermined condition. When a predetermined condition (such as the passing of a predetermined amount of time since the last treatment) is satisfied, the RFID tag 34 can capture energy and direct at least a portion of the energy to an optical energy emitting device 14 to administer treatment to a wound. Thus, it will be understood that in such a method an RFID tag 34 can be configured to selectively direct energy to an optical energy emitting device 14 in response to the data stored in the integrated circuit 42 of the RFID tag 34.

Although embodiments described herein include storing data and information on a memory portion (e.g., the integrated circuit 42) of the RFID tag 34, it will be understood that such data can be stored in any of a variety of other suitable locations. For example, data can be stored on an independent physical memory device coupled to a wound dressing 10. In another example, data can be stored on a memory portion or memory device coupled to or integrated with the circuit board 20 of the optical energy emitting device 14. In yet another example, data can be stored on a memory device that is located remotely from the wound dressing 10. In such an example, data can be transferred to the remote memory device through a physical connection, transmission of radio frequency signals, or other wireless methods.

RFID tags have been generally described and illustrated herein as passive RFID tags. However, an RFID tag can include a number of different arrangements and functionalities. For example, an RFID tag can be an active RFID tag with an independent power source such as a battery or capacitor. Such an active RFID tag wound not need to rely solely on energy from radio frequency transmissions to power optical energy emitting devices. An active RFID tag could partially rely on radio frequency transmission and partially rely on its onboard power supply, or an active RFID could rely solely on its onboard power supply.

Figure 6:
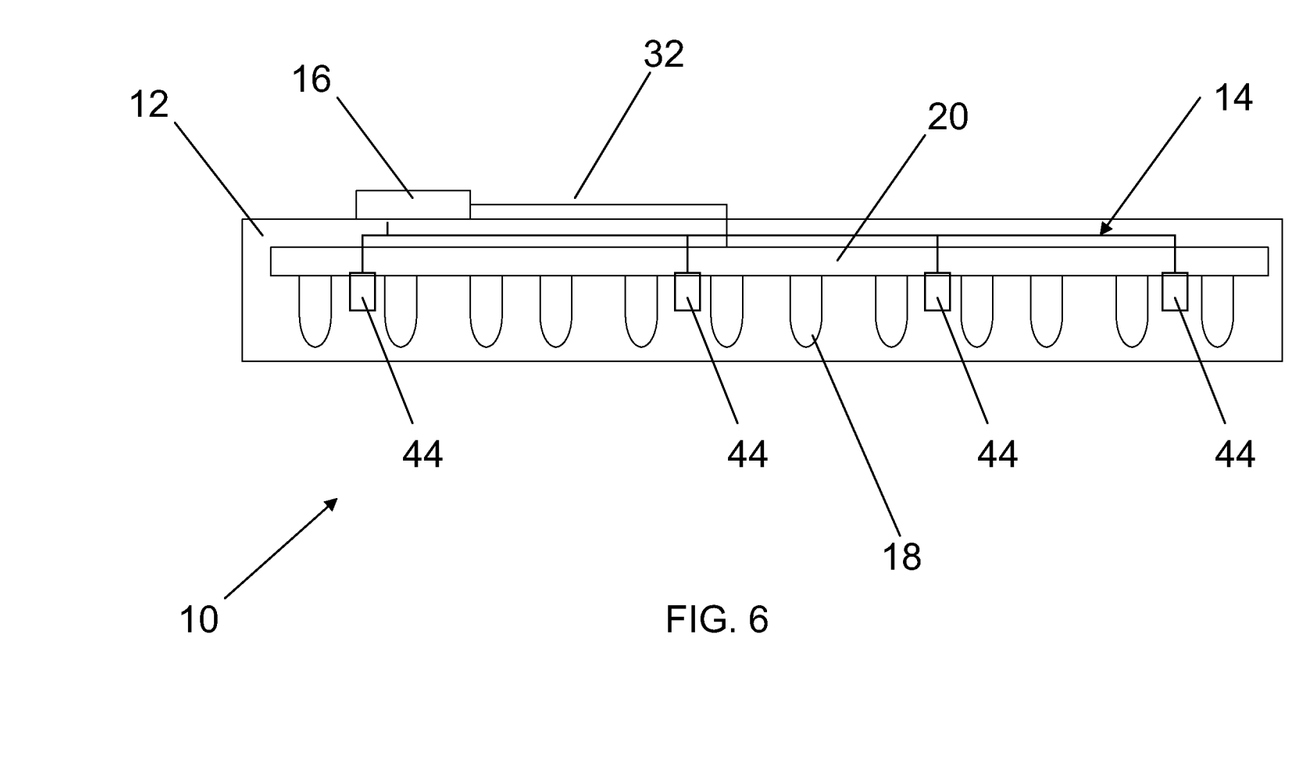
FIG. 6 is another schematic cross-sectional view depicting the wound dressing of FIG. 2.

Other examples of methods for controlling treatments administered to a wound include the use of a biological sensor. As seen in FIG. 6, one or more biological sensors 44 can be attached to the substrate 12 and can be electrically coupled with the radio frequency receiving device 16. The biological sensors 44 can be positioned so that each biological sensor 44 is facing a wound when a wound dressing 10 is positioned over the wound. In one embodiment, the biological sensors 44 can be configured to sense levels of harmful organisms, e.g. bacteria, virus, fungus, present proximate to the biological sensor 44. It will be readily understood by those skilled in the art that when a wound dressing 10 is positioned above and proximate to a wound, the sensors 44 used to detect the harmful organisms can be positioned to sense the organism levels present in the wound or on other biological tissue near or around the wound.

Effective and safe treatment regimens or protocols can establish a threshold level for a permissible bacteria, viral and fungal levels associated with a wound. Such threshold levels can be used in cooperation with sensors 44 to determine when an anti-bacterial, fungal or viral treatment(s) should be administered to a wound. That is to say, when a level of the harmful organisms in a wound is above the threshold level, a treatment can be administered. When the level of harmful organisms in a wound is below the threshold level, a treatment might not be administered. Thus, a biological, fungal or viral sensor 44 can be configured to facilitate the selective administration of treatment when the sensor 44 senses the level of harmful organisms in the wound is above a predetermined threshold level.

Figure 7:
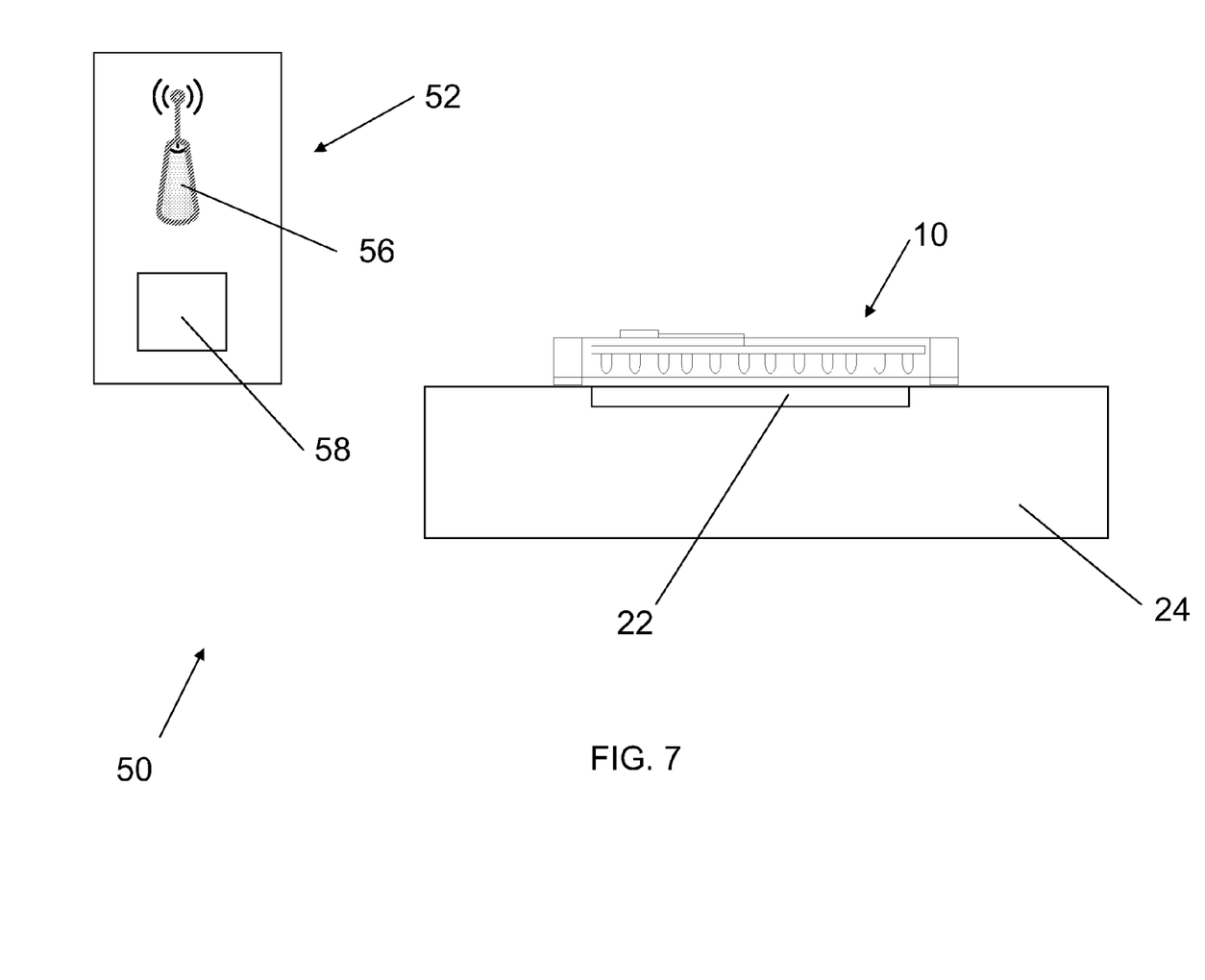
FIG. 7 is a schematic view depicting a wound treatment system in accordance with one embodiment.

Wound dressings 10 can be incorporated into systems for treating wounds. As seen in FIG. 7, in one embodiment, a wound treatment system 50 includes a radio frequency transceiver 52 and a wound dressing or wound treatment dressing 10 positioned remotely from the radio frequency transceiver 52. The radio frequency transceiver 52 can be configured to generate radio frequency transmissions. The radio frequency transceiver 52 can include a radio signal transmitter 56 to transmit radio signals (i.e., radio frequency transmissions). A radio frequency transceiver 52 can function as an RFID reader that retrieves information from one or more wound treatment dressings (e.g., 10) by transmitting radio signals that are modulated and reflected by the wound treatment dressings (e.g., 10) and subsequently read by the radio frequency transceiver 52. The radio frequency transceiver 52 can also function as a source of energy for the radio frequency receiver device 16 of the wound treatment dressing (e.g., 10). For example, similar to previous descriptions, a radio frequency transceiver 52 can transmit relatively high energy radio signals that can be captured by an RFID tag 34 of the wound dressing 10 and can be directed to power either the RFID tag 34 or other devices such as LEDs 18 or biological sensors 44.

A wound treatment dressing 10 of FIG. 7 can be generally configured as described above, where the wound treatment dressing 10 includes a substrate 12 configured to engage biological tissue of a patient, an optical energy emitting device 14 attached to the substrate 12, and a radio frequency receiving device 16 electrically coupled with the optical energy emitting device 14. The radio frequency receiving device 16 can be configured to capture energy from the radio frequency transmissions and can be further configured to direct at least a portion of the energy to the optical energy emitting device 14. Upon receipt of the energy from the radio frequency receiving device 16, the optical energy emitting device 14 can emit light onto the biological tissue of a patient.

A wound treatment system 50 can be configured to evaluate data for one or more responding wound treatment dressings 10 to control the treatments administered by each wound treatment dressing 10. In one embodiment, the radio frequency receiving device 16 comprises the RFID tag 34 that includes a memory device such as an integrated circuit 42. The integrated circuit 42 can store an identifying marker that uniquely identifies the RFID tag 34, and thus, uniquely identifies the wound treatment dressing 10 associated with the RFID tag 34. The RFID tag 34 and integrated circuit 42 can also be configured to communicate with the radio frequency transceiver 52 in response to radio frequency transmissions generated by the transceiver 52. For example, the RFID tag 34 can transmit the identifying marker to the radio frequency transceiver 52 in response to a radio frequency transmission. When the identifying marker is transmitted to the radio frequency transceiver 52, the transceiver 52 can identify the wound treatment dressing 10 with which it is communicating.

In one embodiment, the radio frequency transceiver 52 further includes a memory device 58 for storing data and information. Such a memory device 58 can store data associated with RFID tags 34 that communicate with the transceiver 52. For example, the memory device 58 can store the identification marker of a RFID tag 34 and can also store data corresponding to the administration of treatments to a wound by the wound treatment dressing associated with the RFID tag 34. By storing such data, the radio frequency transceiver 52 can store a history of treatments administered by specific wound treatment dressing 10.

In one embodiment, the radio frequency transceiver 52 can be configured to send a first radio frequency transmission to a wound treatment dressing 10. The first radio frequency transmission can have enough energy to facilitate the reading of the identifying marker from the RFID tag 34 of the wound treatment dressing 10. The first radio frequency transmission energizes the RFID tag 34. The RFID tag 34 modulates and encodes the first frequency radio transmission with the identifying marker. A portion of the first frequency radio transmission is reflected back to the radio frequency transceiver 52. The radio frequency transceiver 52 demodulates the reflected portion of the first radio frequency transmission and reads the identifying marker encoded on the reflected portion of the first radio frequency transmission. However, the first radio frequency transmission might not have enough energy to provide for the RFID tag 34 to administer a treatment to a wound.

Once the radio frequency transceiver 52 reads the identifying marker and identifies the wound treatment dressing 10, the radio frequency transceiver 52 evaluates the treatment history of the identified wound treatment dressing 10. Such treatment history can be stored in the memory device 58 of the radio frequency transceiver 52. Alternatively, a treatment history can be stored in the in the integrated circuit 42.

Similar to previous descriptions, a treatment regimen can include a predetermined condition such as a specified amount of time between treatments. The radio frequency transceiver 52 can evaluate or calculate the time of the last administered treatment and determine if enough time has passed since the last administered treatment. If an appropriate amount of time has not passed, the radio frequency transceiver 52 can remain idle until the appropriate amount of time has passed. Once this time passes, the transceiver 52 can transmit a second radio frequency transmission that has enough energy for the wound treatment dressing 10 to administer a treatment to the wound. The radio frequency transceiver 52 can then store data related to this initiated treatment for future retrieval and use.

Similarly, if the wound treatment dressing 10 includes a sensor 44 for the detection of harmful organisms, e.g. bacteria, virus, fungus, the radio frequency transceiver 52 can be configured to evaluate the level of the organisms in the wound prior to transmitting a radio frequency transmission with enough energy to administrate a treatment to eliminate the harmful organisms. For example, the transceiver 52 can transmit a first radio frequency transmission with enough energy to power a sensor 44 for detecting harmful organisms to read or sense the organism level in the wound and return that reading to the radio frequency transceiver 52. The radio frequency transceiver 52 can evaluate the organism level reading against a predetermined threshold based on a treatment regimen or protocol. If the organism level is below the threshold, the radio frequency transceiver 52 can remain idle until the next reading of the organism level in the wound. If the organism level is above the threshold, the radio frequency transceiver 52 can transmit a second radio frequency transmission that has enough energy for the wound treatment dressing 10 to administer another treatment to the wound.

The wound treatment system 50 can be used or initiated in a variety of ways. For example, a patient fitted with a wound treatment dressing 10 can periodically approach a stationary radio frequency transceiver 52 and activate the radio frequency transceiver 52. The radio frequency transceiver 52 can evaluate the treatment history or level of harmful organisms as described above. If it is determined that a treatment is required or desired, the radio frequency transceiver 52 can transmit a radio signal with enough energy to facilitate administer of treatment to the wound. In this example, the radio frequency transceiver 52 can be a low cost transceiver 52 that is purchased for home use by the patient. In a further example similar to that above the radio frequency transceiver capable of communicating with the dressing may be part of an electronic device commonly carried by a consumer or health care professional, such as a mobile phone, PDA or other transmitting device. In this example an assessment of the wound condition may be triggered by a message from a doctor or health care professional, asking the patient to place the device near the dressing; if a sensor is present, the requirement for a treatment can be assessed remotely via the mobile phone communication link and triggered by that link. Alternatively, in the event that the infection requires more assistance, the user may be requested to see their health care professional. In another example, a radio frequency transceiver 52 can be automated to send out periodic radio frequency transmissions and evaluate all wound treatment dressings (e.g., 10) within its signal range. If it is determined that any of the wound treatment dressings (e.g., 10) require a treatment, the radio frequency transducer 52 can send out a signal to those wound treatment dressings (e.g., 10) to initiate treatment of the wound. In this example, the radio frequency transceiver 52 can be a commercial transceiver 52 such as for use by hospitals, nursing homes, and other such facilities to provide treatment to multiple patients. It will be understood that embodiments as described herein can be used by consumers, patients, or institutions in a home setting or be used by consumers, patients, or institutions in a professional setting.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art.

What is claimed is:

1. A wound dressing comprising: a substrate configured to engage biological tissue of a patient;
   an optical energy emitting device attached to the substrate; and a radio frequency receiving device electrically coupled with the optical energy emitting device,
   the radio frequency receiving device being configured to capture energy from a radio frequency transmission and being further configured to direct at least a portion of the energy to the optical energy emitting device;
   a biological sensor attached to the substrate and electrically coupled with the radio frequency receiving device; and
   wherein, upon receipt of the directed portion of the energy from the radio frequency receiving device, the optical energy emitting device is configured to emit light onto biological tissue of a patient.

2. The wound dressing of claim 1, wherein the substrate includes an adhesive layer configured to removably secure the wound dressing to biological tissue of a patient.

3. The wound dressing of claim 1, wherein the optical energy emitting device includes a light emitting diode.

4. The wound dressing of claim 3, wherein the light emitting diode is configured to emit ultraviolet light.

5. The wound dressing of claim 1, wherein the optical energy emitting device includes an array of light emitting diodes arranged in a matrix.

6. The wound dressing of claim 1, wherein the radio frequency receiving device includes a radio frequency identification tag having a memory device.

7. The wound dressing of claim 6, wherein the memory device is configured to store data corresponding to the energy directed from the radio frequency receiving device to the optical energy emitting device.

8. The wound dressing of claim 7, wherein the radio frequency receiving device is configured to selectively direct energy to the optical energy emitting device in response to the data stored in the memory device.

9. The wound dressing of claim 1, wherein the biological sensor is configured to sense a level of bacteria, virus or fungi present on biological tissue of a patient proximate to the biological sensor.

10. The wound dressing of claim 9, wherein the biological sensor is configured to facilitate direction of energy from the radio frequency receiving device to the optical energy emitting device when the level of bacteria, virus or fungi activity sensed by the biological sensor is above a threshold level.

11. A wound treatment system comprising:
    a radio frequency transceiver configured to generate radio frequency transmissions;
    a wound treatment dressing remote from the radio frequency transceiver, the wound treatment dressing comprising:
      a substrate configured to engage biological tissue of a patient;
      an optical energy emitting device attached to the substrate; and
      a radio frequency receiving device electrically coupled with the optical energy emitting device, the radio frequency receiving device being configured to capture energy from a radio frequency transmission and being further configured to direct at least a portion of the energy to the optical energy emitting device;
      a biological sensor attached to the substrate and electrically coupled with the radio frequency receiving device; and
      wherein, upon receipt of the directed portion of the energy from the radio frequency receiving device, the optical energy emitting device is configured to emit light onto biological tissue of a patient.

12. The wound treatment system of claim 11, wherein the radio frequency receiving device includes a radio frequency identification tag having a memory device.

13. The wound treatment system of claim 12, wherein the memory device is configured to store an identifying marker for the radio frequency identification tag and to transmit the identifying marker to the radio frequency transceiver in response to the radio frequency transmission.

14. The wound treatment system of claim 13, wherein:
the radio frequency receiving device is configured to transmit data to the radio frequency transceiver in response to the radio frequency transmission, wherein the data corresponds to energy directed from the radio frequency receiving device to the optical energy emitting device; and
the radio frequency transceiver is configured to collect and associate the data with the radio frequency identification tag.

15. A method of treating a wound comprising:
positioning a wound treatment dressing proximate to biological tissue of a patient, wherein the wound treatment dressing comprises a substrate, an optical energy emitting device attached to the substrate, a biological sensor attached to the substrate and electrically coupled with the radio frequency receiving device, and a radio frequency receiving device electrically coupled with the optical energy emitting device;
positioning a radio frequency transceiver within signal range of the wound treatment dressing;
generating a radio frequency transmission with the radio frequency transceiver;
capturing by the radio frequency receiving device energy from the radio frequency transmission to facilitate energizing of the radio frequency receiving device; and
directing at least a portion of the energy from the radio frequency receiving device to the optical energy emitting device such that the optical energy emitting device emits light through the substrate and onto biological tissue of a patient.

16. The method of claim 15, further comprising storing data within at least one of the radio frequency receiving device and the radio frequency transceiver, wherein the data corresponds to a past instance of directing energy from the radio frequency receiving device to the optical energy emitting device.

17. The method of claim 16, wherein energy from the radio frequency receiving device is selectively directed to the optical energy emitting device in response to the data.

18. The method of claim 15, further comprising storing an identifying marker within the radio frequency receiving device and selectively transmitting the identifying marker from the radio frequency receiving device to the radio frequency transceiver in response to the radio frequency transmission.

19. The method of claim 15, further comprising:
sensing a level of bacteria, viral or fungal in the wound; and
comparing the sensed level of bacteria, viral or fungal in the wound with a threshold level of bacteria, viral or fungal; and
wherein energy is directed from the radio frequency receiving device to the at least one optical energy emitting device only when the sensed level of bacteria, viral or fungal in the wound is above a threshold level of bacteria, viral or fungal.

20. The method of claim 19, wherein the radio frequency transceiver is configured to broadcast a larger amount of energy to the radio frequency receiving device when the sensed level of bacteria, viral, or fungal in the wound is above a threshold level of bacteria, viral, or fungal.

* * * * *